(12) United States Patent
Poeschmann et al.

(10) Patent No.: US 6,352,560 B1
(45) Date of Patent: Mar. 5, 2002

(54) JOINT PROSTHESIS

(75) Inventors: Paul Henricus Poeschmann, Amersfoort; Cornelis Marinus Van Leeuwen, Etten-Leur, both of (NL)

(73) Assignee: Van Straten Beheer B.V., Nieuwegein (NL)

( * ) Notice: Subject to any disclaimer, the term of this patent is extended or adjusted under 35 U.S.C. 154(b) by 0 days.

(21) Appl. No.: 09/720,983

(22) PCT Filed: Jul. 2, 1999

(86) PCT No.: PCT/NL99/00413

§ 371 Date: Jan. 3, 2001

§ 102(e) Date: Jan. 3, 2001

(87) PCT Pub. No.: WO00/01327

PCT Pub. Date: Jan. 13, 2000

(30) Foreign Application Priority Data

Jul. 3, 1998 (NL) .............................................. 1009550

(51) Int. Cl.[7] .................................................. A61F 2/36
(52) U.S. Cl. ................. 623/23.4; 623/21.11; 623/21.15; 623/21.16
(58) Field of Search ........................... 623/21.15, 21.16, 623/21.17, 21.11, 21.12, 23.39, 23.4, 18.11, 23.11, 63, 64

(56) References Cited

U.S. PATENT DOCUMENTS

| 3,805,302 | A | * | 4/1974 | Mathys .................... 623/18.11 |
| 3,990,118 | A |   | 11/1976 | Strickland et al. |
| 3,991,425 | A |   | 11/1976 | Martin et al. |
| 5,007,932 | A |   | 4/1991 | Bekki et al. |
| 5,047,059 | A | * | 9/1991 | Saffar ...................... 623/21.15 |
| 5,290,314 | A | * | 3/1994 | Koch et al. .............. 623/21.16 |
| 5,674,297 | A |   | 10/1997 | Lane et al. |
| 5,984,971 | A | * | 11/1999 | Facciioli et al. ......... 623/18.11 |

FOREIGN PATENT DOCUMENTS

| DE | 28 14 752 A1 | 10/1978 |
| DE | 195 12 854 C1 | 8/1996 |
| EP | 0 572 339 A1 | 12/1993 |
| GB | 1 530 301 | 10/1978 |

* cited by examiner

Primary Examiner—Pedro Philogene
(74) Attorney, Agent, or Firm—Young & Thompson

(57) ABSTRACT

The joint prosthesis includes a first part with a cylindrical socket and a second part with a cylindrical head. The cylindrical head and socket are of complementary form, in such a manner that together they are able to form a linear hinge. The cylindrical socket extends over at most 180° in the circumferential direction. The cylindrical head is provided with a radial thickened section which extends in the circumferential direction. The cylindrical socket is provided with a radial recess which extends in the circumferential direction and in which the radial thickened section can be accommodated, with the cylindrical head in bearing contact inside the cylindrical socket. The radial thickened section and radial recess are arranged centrally and are formed so as to be self-aligning with respect to one another. The cylindrical head may be arranged on at least one support arm and one or both longitudinal edges of the cylindrical socket may be provided, in the arca of the at least one support arm, with a cutout in which the support arm can be completely or partially accommodated.

19 Claims, 3 Drawing Sheets

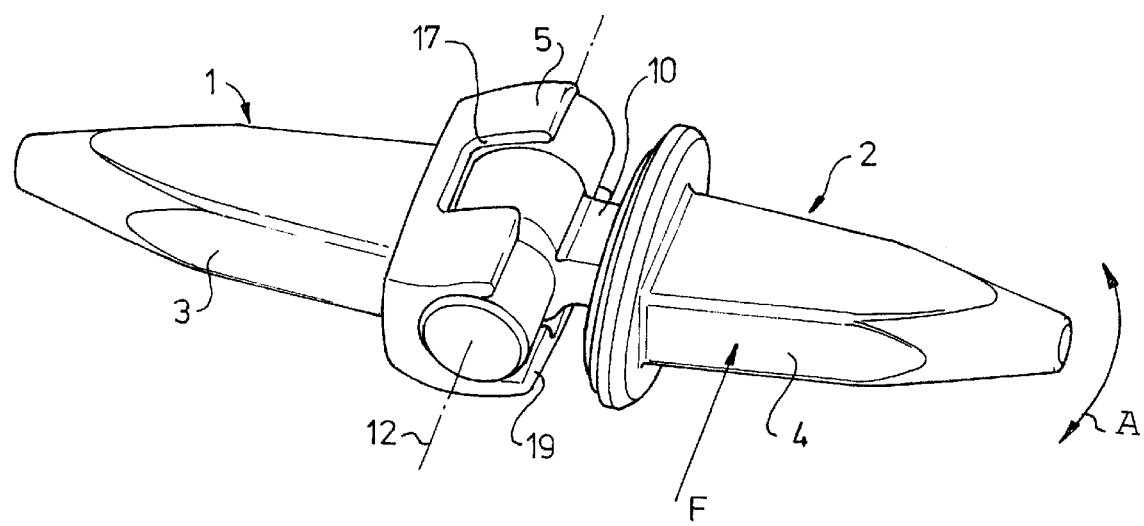
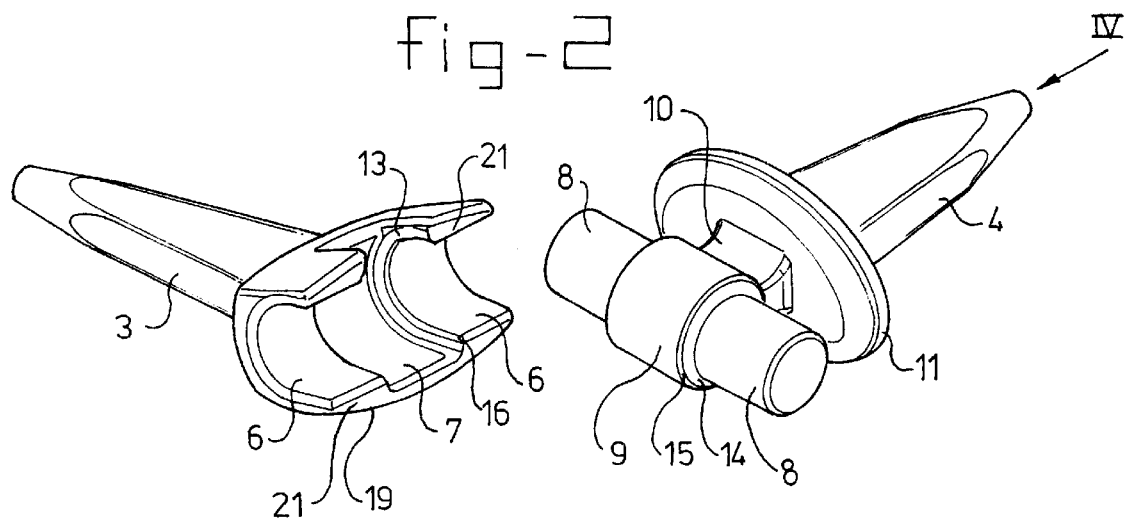

JOINT PROSTHESIS

FIELD OF THE INVENTION

The present invention relates to a joint prosthesis comprising a first part with a cylindrical socket and a second part with a cylindrical head, the cylindrical head and socket being complementary to one another, in such a manner that together they are able to form a linear hinge which extends in the longitudinal direction of the head/socket.

BACKGROUND OF THE INVENTION

A prosthesis of this nature is known, in the form of a finger joint prosthesis, from U.S. Pat. No. 3,991,425. A prosthesis of this nature, of at least a prosthesis which appears extremely similar, is also known under the name Djoa prosthesis. The Djoa prosthesis comprises a cylindrical roll surface in which a slot is formed. A hollow cylindrical socket runs over the cylindrical roll surface, with a projection which projects out of the socket fitting into the slot. The purpose of this projection is to prevent the socket from moving sideways, i.e. in the longitudinal direction of the linear hinge, with respect to the cylindrical roll surface, in order to ensure stability of the joint prosthesis in relation to loads which act in the longitudinal direction of the hinge. However, a drawback of this design is that in the event of such loads a force is exerted on the underlying bones to which the joint is attached, via the slot with the projection situated therein. As a result, the stems may be dislodged from the underlying bone or may break off, which would lead to considerable damage to the underlying bone.

GB patent specification 1,530,301 has disclosed a finger prosthesis which differs from the joint prosthesis according to the present invention in particular by the fact that the socket parts are fixed to the head parts by means of a snap-action connection, i.e. the socket parts extend over more than 180°, as is clear from the figures. Owing to the snap-action connection, this prosthesis, in the implanted position, does not allow any movement of the prosthesis parts with respect to one another apart from the pivoting movement about the longitudinal axis of the head parts/ socket parts. It is not possible for the prosthesis parts to move apart from one another and to pivot with respect to one another transversely to the hinge direction.

DE-Offenlegungsschrift 2,814,752 has disclosed a two-part joint prosthesis, in which the first part comprises a fork with a socket part inside. The second part is provided with a head part which can be fixed to the socket part by means of a snap-action connection. Since the head part is of spherical or convex design, and the socket part is shaped accordingly, this joint prosthesis has two degrees of freedom. In addition to the main hinged movement, limited pivoting with respect to the main hinged movement is also possible. The prosthesis disclosed by DE-2,814,752 cannot move apart in the implanted position.

SUMMARY OF THE INVENTION

The object of the present invention is to provide a joint prosthesis which, on the one hand, provides so-called medial/lateral stability, so that it is impossible for the moving parts to move in the longitudinal direction of the hinge with respect to one another, and, on the other hand, allows transverse forces, acting in the longitudinal direction of the hinge, on the bones which are connected by the joint without this inevitably leading to excessive load on the connection between the joint parts and the respective bones to which they are attached.

According to the invention, this object is achieved by means of a special design of the joint prosthesis, and in particular by the fact that:

the cylindrical socket extends over at most 180° in the circumferential direction, the cylindrical head is provided with a radial thickened section which extends in the circumferential direction, and the cylindrical socket is provided with a radial recess which extends in the circumferential direction and in which the radial thickened section can be accommodated, preferably with the cylindrical head bearing inside the cylindrical socket.

In this design, since the cylindrical socket extends over at most 180°, the cylindrical head can be removed from the cylindrical socket by pulling it out in a direction which is parallel to or lies between the tangents at the free ends of the extent of the cylindrical socket. When the bone to which the cylindrical socket is attached extends in this direction, this essentially means that this bone is pulled away from the joint in its longitudinal direction. However, this also means that when, in this position, a transverse force which is directed in the longitudinal direction of the linear hinge acts on the said bone, this bone can undergo a pivoting movement, during which the cylindrical head comes out of the socket at one end of the linear hinge and is pressed against the socket at the other end of the linear hinge. Consequently, the action of such a transverse force on the connection between the prosthesis parts with the respective bones is reduced considerably. These transverse forces can then be absorbed entirely by the natural, or possibly artificial, ligaments which hold the joint together. If the cylindrical socket extends over less than 180°, the area in which such a tilting movement of the bone which is attached to the cylindrical socket with respect to the linear hinge can take place will be increased in size, as will be clear. However, an important advantage of the joint prosthesis according to the invention is that this so-called tilting freedom which has been outlined above decreases as the bone which is attached to the cylindrical head is situated further and further outside the area defined by the tangents at the free ends of the cylindrical head. Depending on the exact orientation of the cylindrical socket with respect to the underlying bone to which this socket is attached, a moment with respect to the longitudinal axis of the said bone will act on the said bone. Such a rotation can then be absorbed, in the case where there is a joint at the other end of the said bone, by the said joint or by the ligaments associated with the said joint. Generally, the cylindrical socket will be oriented in such a manner, with respect to the bone to which it is attached, that the cylindrical head can be removed from this socket when the two bones are situated essentially in line with one another. As will be clear to a person skilled in the art, such a joint prosthesis according to the invention can generally be used with very great success for finger joint prostheses, toe joint prostheses, and possibly elbow or knee prostheses.

In order to achieve a so-called pivoting freedom or tilting freedom of the joint prosthesis which is equal in both opposite directions (also known in the specialist medical field as the medial and lateral directions), it is advantageous, according to the invention, if the radial thickened section and the radial recess are arranged centrally, as seen in the longitudinal direction of the linear hinge.

In order to ensure that after a so-called tilting or pivoting of the joint parts with respect to one another, the cylindrical head moves correctly back into the cylindrical socket (i.e. with their cylinder axes essentially coinciding), it is advantageous, according to the invention, if the radial thickened section and/or the radial recess are formed so as to be self-aligning with respect to one another. It will be clear to a person skilled in the art that a self-aligning effect of this nature can be achieved in a wide variety of ways by suitable shaping of circumferential sides, which extend in particular in the circumferential direction, of the radial thickened section and/or the radial recess. According to the invention, the self-aligning effect can be achieved, inter alia, by providing the circumferential sides of the radial thickened section with bevels and/or rounded portions, optionally in combination with bevels and/or rounded portions on the circumferential sides of the radial recess.

In order, on the one hand, to provide sufficient medial/lateral stability, i.e. resistance to displacement of the joint-prosthesis parts with respect to one another in the longitudinal direction of the linear hinge and, on the other hand, to allow the radial thickened section and the radial recess to be self-aligning with respect to one another, it is advantageous, according to the invention, if the circumferential sides, which extend in the circumferential direction, of the radial thickened section and/or of the radial recess comprise an active circumferential side face which includes an angle of approximately 1° to approximately 10° with a radially oriented transverse plane. These side faces therefore do not extend at right angles to the axis of rotation of the linear hinge, but rather at a relatively small angle with respect to a radial transverse plane which is perpendicular to the said hinge axis.

In order to be able to increase the maximum freedom of rotation of the joint prosthesis with respect to the maximum freedom of rotation permitted by the extent of the cylindrical head itself (also known in the medical field as the flexural freedom), it is advantageous according to the invention, in the case where the cylindrical head is arranged on the end of at least one support arm which extends radially with respect to the cylindrical head, if one or both longitudinal edge(s) of the cylindrical socket are provided, in the area of the at least one support arm, with a cutout in which the cross section of the support arm can be completely or partially accommodated.

In order to prevent the functioning or effectiveness of the natural ligaments which hold the joint (in this case the joint prosthesis) together from decreasing, it is advantageous, according to the invention, if the freedom of rotation of the linear hinge in one or both direction(s) of rotation is greater than the associated freedom of rotation (medical: flexural freedom) of the natural joint which the joint prosthesis is intended to replace. This ensures that the freedom of rotation is limited not by the joint prosthesis but by the original, natural or possibly completely or partly artificial ligaments. The extent to which this freedom of rotation of the joint prosthesis is greater than that of the natural joint will preferably be approximately 5° to approximately 20°, such as for example, and more preferably, approximately 15°.

In order in particular to design the joint prosthesis to be extremely small while nevertheless able to withstand high loads, it is advantageous, according to the invention, if the first part and the second part are each a metal part, for example are each a single-piece metal part. It is thus possible to produce joint prostheses which, in relative terms, are extremely small and yet strong, such as for example finger joint prostheses. The metal parts are in this case preferably made from a chromium-cobalt alloy, as is known per se from the prior art for prostheses and joint prostheses.

In order to improve the friction properties at the contact surfaces of the joint-prosthesis parts which can move with respect to one another, it is advantageous, according to the invention, if the first part and the second part, or at least the contact surfaces of the cylindrical head and cylindrical socket, are coated with a suitable coating material.

In order to counteract rejection and other undesirable interactions between the joint prosthesis and the surrounding human or animal tissue, it is advantageous, according to the invention, if the first and second parts, or at least their external surfaces, are made from or coated with a material which is compatible with the human, or if appropriate animal, body, i.e. in particular a material which is compatible with the human, or if appropriate animal, body without entering into chemical reactions therewith, or at least without entering into any adverse and/or undesirable chemical reactions therewith.

Since in many joints a so-called tilting or pivoting freedom is desirable or required only within a limited rotational position of the adjoining bones with respect to one another, it is advantageous, according to the invention, if the cylindrical socket extends over at least 160°, preferably over at least 170°, in the circumferential direction.

The joint prosthesis according to the invention can be used in particular as a finger joint prosthesis, such as an MCP prosthesis (MCP=metacarpophalangeal) or in particular a PIP prosthesis (PIP=proximal interphalangeal). Although prostheses are used relatively infrequently at the DIP joint (DIP=distal interphalangeal), since they are deemed less useful, it should be noted that the joint prosthesis according to the invention can also be used with considerable success as a DIP prosthesis. The same comments as those made in relation to the DIP prosthesis should also be noted in relation to toe joint prostheses, for which the joint prosthesis according to the invention can also be used with considerable success.

Depending on the specific location where the joint prosthesis according to the invention is used, it will be possible to adapt the orientation of the cylindrical socket with respect to the bone which is to be connected thereto, as well as the extent in the circumferential direction of the cylindrical socket, as well as the one or more cutouts for accommodating the support arm, in order to increase the freedom of rotation of the joint prosthesis in relation to the freedom of rotation permitted by the cylindrical socket.

BRIEF DESCRIPTION OF THE DRAWINGS

In the following text, the present invention will be explained in more detail with reference to examples illustrated in the drawings, in which:

FIG. 1 shows a perspective view of a joint prosthesis according to the invention in the so-called extended state;

FIG. 2 shows a perspective view of the embodiment shown in FIG. 1, but with the parts of the joint prosthesis taken apart;

DETAILED DESCRIPTION OF THE INVENTION

Figure 3:
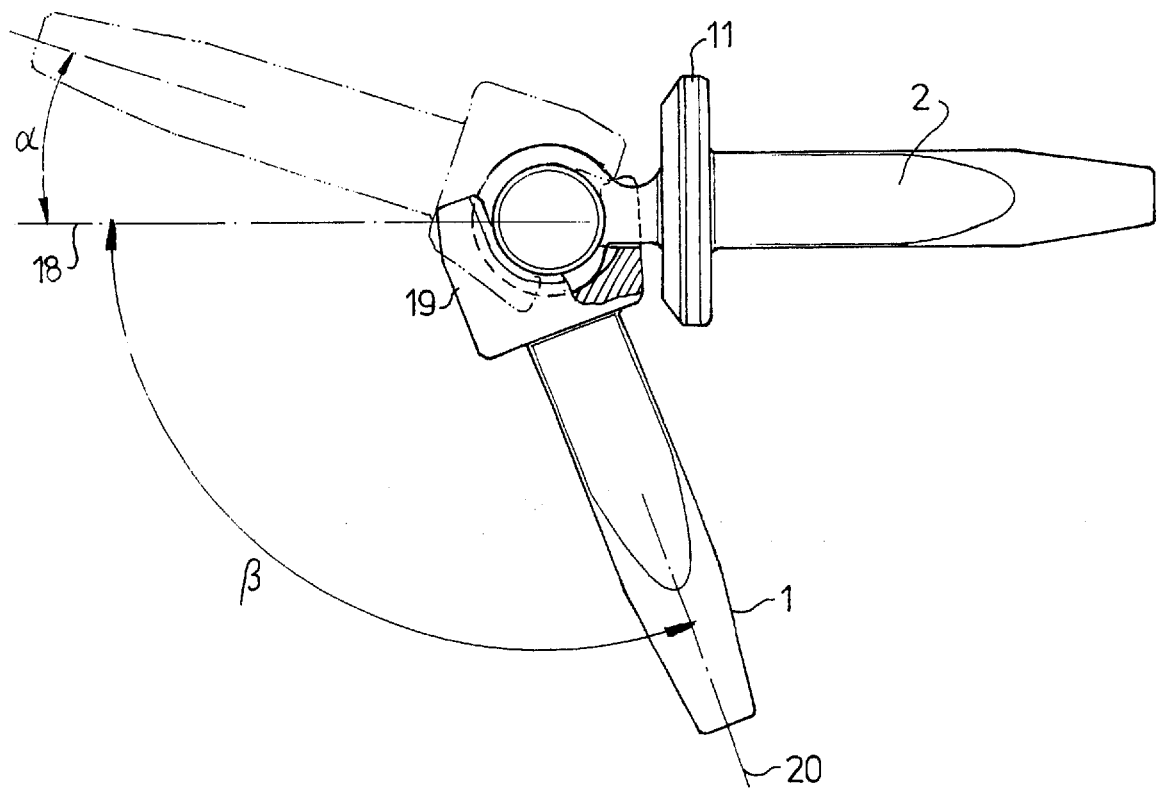
FIG. 3 shows a side view, partially in section, of a joint prosthesis in accordance with the embodiment shown in FIGS. 1 and 2 which has been pivoted into a limit position.
Figure 4:
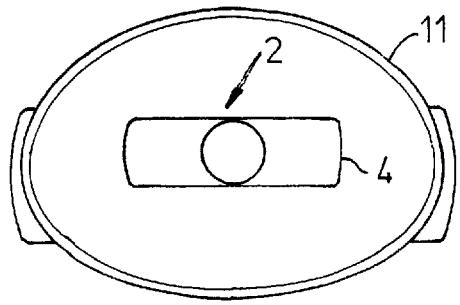
FIG. 4 shows a rear view, from the direction of arrow IV, of one part of the joint prosthesis according to the invention.

FIG. 1 shows a diagrammatic, perspective view of a so-called PIP prosthesis, the view being from above onto the underside, in the implanted position, of the joint prosthesis, i.e. the side which lies on the inside of the hand in the implanted position. In this case, joint part 1 is the proximal joint part, which lies on the carpal (metacarpal) side of the joint, i.e. that side of the joint which is directed towards the hand. The joint part 2 is the distal joint part which lies on that side of the joint which is directed towards the fingertips. Both joint parts comprise a stem which is known per se, or at least is nothing special, and by means of which the joint prosthesis can be attached in a respective phalangeal bone of the hand using techniques which are known per se. It is entirely within the scope of the invention for these stems 3 and 4 also to be of different design, for example as a multiple stem for mutually parallel pins or with a different shape from that which is illustrated in the figures.

The proximal part 1 is provided with a head 5, in which a cylindrical socket 6 is formed. The centre of the cylindrical socket 6 is provided with a recess 7 which extends in the circumferential direction of the cylindrical socket 6, divides the cylindrical socket 6 in two and is likewise of cylindrical form. This recess 7 thus forms, as it were, a deeper, additional cylindrical socket surface between the two parts of the cylindrical socket 6. The cylindrical socket 6, or at least its purely central part, extends over 175 to 180°, and will preferably extend over approximately 180°.

The distal part 2 of the joint prosthesis is provided with a cylindrical head 8 which extends essentially over 360° and is provided in its centre with a radial thickened section 9 which extends over virtually the entire circumference of the cylindrical head 8. Those parts of the cylindrical head 8 which lie next to the central thickened section extend over 360°. The radial thickened section 9 extends over less than 360°, since it is interrupted by a support arm 10, via which the cylindrical head 8, 9 is connected to the stem 4. An oval flange 11 is formed between the support arm 10 and the stem 4, providing support on the underlying bone and preventing the distal part 2 of the joint prosthesis from being pressed too deep into the associated bone.

The cylindrical head 8 and cylindrical socket 6 are shaped so as to complement one another, in such a manner that the cylindrical head 8 can be accommodated in the cylindrical socket 6 and can execute a hinged movement about the common, describing cylinder axis. In this case, the width of the thickened section 9, as seen in the direction of the hinge axis 12, i.e. in the longitudinal direction of the head/socket, is essentially equal to the width of the recess 7 in the cylindrical socket 6, as seen in the same direction. Furthermore, the thickened section 9 is dimensioned in such a manner that it can be accommodated entirely inside the recess 7, in which position there is no need for the cylindrical circumferential surfaces, which run parallel to the longitudinal direction, of the recess and the thickened section as such to be in contact with one another. It will be clear that the thickened section 9 thus prevents the distal joint prosthesis part 2 from being displaced in the longitudinal direction of the linear hinge with respect to the proximal joint prosthesis part 1, since the essentially radial circumferential side faces 14 of the thickened section 9 and the essentially radial circumferential side faces 13 of the recess will be in contact, or virtually in contact, with one another.

The distal joint prosthesis part 2 may execute a pivoting movement, in the direction of arrow A, with respect to the proximal joint prosthesis part 1, in which case one end of the cylindrical head 8 will come out of the cylindrical socket 6 and the other, opposite end of the cylindrical head 8 will be pressed into the cylindrical socket 6. In this way, a force which acts on the distal phalangeal bone of the hand in the transverse direction, indicated by arrow F, can result in tilting or pivoting, in the direction of arrow A, of the distal joint prosthesis part 2 with respect to the proximal joint prosthesis part 1, without this leading to a load being imposed on the connection between the stems 3 and 4 and the proximal phalangeal bone of the hand or distal bone of the hand, since the pivoting indicated by arrow A and caused by the transverse force F is then absorbed by the natural or artificial joint ligaments.

In order, after such pivoting of the distal joint prosthesis part 2 with respect to the proximal joint prosthesis part 1 in the direction of arrow A, to ensure that the cylindrical head moves correctly into the cylindrical socket, in particular the thickened section moves correctly into the recess, under the influence of the restoring force exerted by the joint ligaments, the thickened section and/or recess are preferably both shaped so as to be self-aligning. According to the invention, this can be achieved, inter alia, by bevelling the circumferential sides 14 of the thickened section 9 at 15 and by bevelling the circumferential sides 13 of the recess 7 at 16. According to the invention, the self-aligning action can be improved further by providing the circumferential sides 14 circumferential side faces which slope slightly towards one another in the radially outward direction, for example each slope at an angle of from 1 to 10° with respect to a transverse plane which is perpendicular to the hinge axis 12. In a corresponding way, the circumferential sides of the recess can be provided with circumferential side faces which slope towards one another in the same direction, also preferably at an angle of from 1 to 10° with respect to a transverse plane which is perpendicular to the hinge axis 12.

As can be seen from FIGS. 1, 2 and 3, the longitudinal edge (21) of the cylindrical socket 6 is provided with a cutout 17 on its underside, which is shown as the top side in FIG. 1 and as the underside in FIG. 3. The dimensions of the cutout 17 are such that it is able to accommodate the support arm 10, so that the freedom of rotation of the distal joint prosthesis part 2 with respect to that of the proximal joint prosthesis part 1 is made greater than the extent in the circumferential direction of the cylindrical socket would inherently allow. In this way, it is possible for the distal joint prosthesis part 2 to be over-extended, by an angle $\alpha$ of 25°, in the upwards direction with respect to the extended position illustrated in FIG. 3 by the axis 18 (in the medical field, this is also known by the term hyperextension), and also that the distal joint prosthesis part 2 can rotate downwards, in the anticlockwise direction, over an angle $\beta$ of 125° in the downwards direction (also known in the medical field by the term flection).

Figure 5:
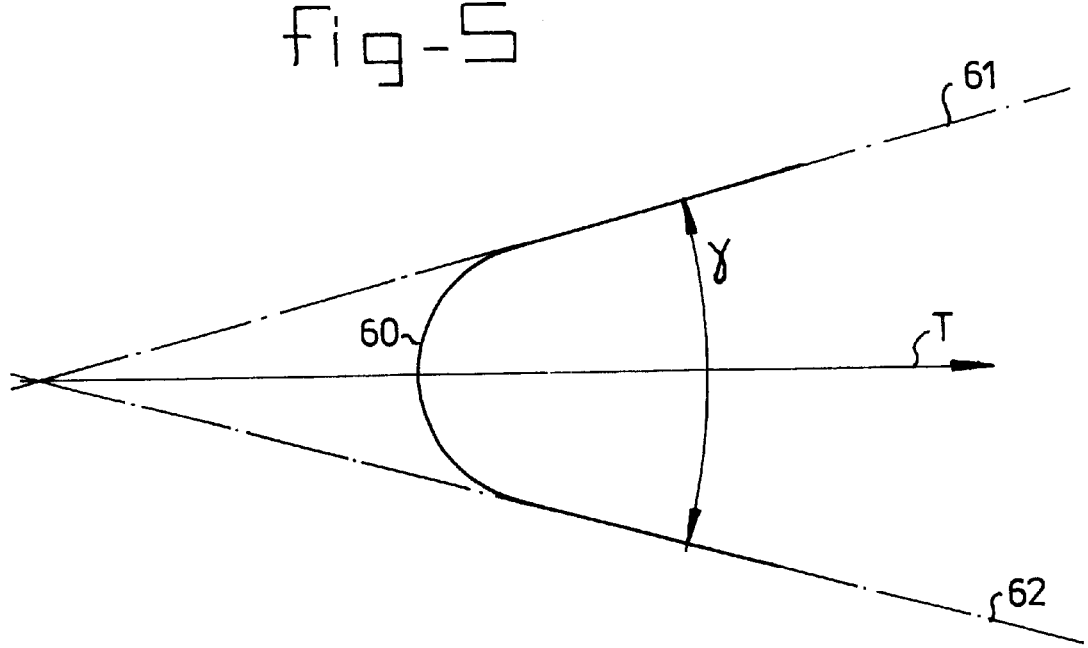
FIG. 5 shows an extremely diagrammatic sketch of the cylindrical socket, on the basis of which the directions in which the cylindrical head can be removed from the cylindrical socket are indicated.

FIG. 5 provides a very diagrammatic side view of a cylindrical socket which extends over 150° in the circumferential direction. 61 and 62 are in this case the tangents on the opposite ends of the cylindrical extent of the socket 60. These tangents 61 and 62, with their intersection point, together determine a range $\gamma$ of tension directions T via which the cylindrical head can be pulled out of the cylindrical socket. The arrow T in this case runs within the tangent lines 61 and 62 and intersects the intersection of these tangents.

Figure 6:
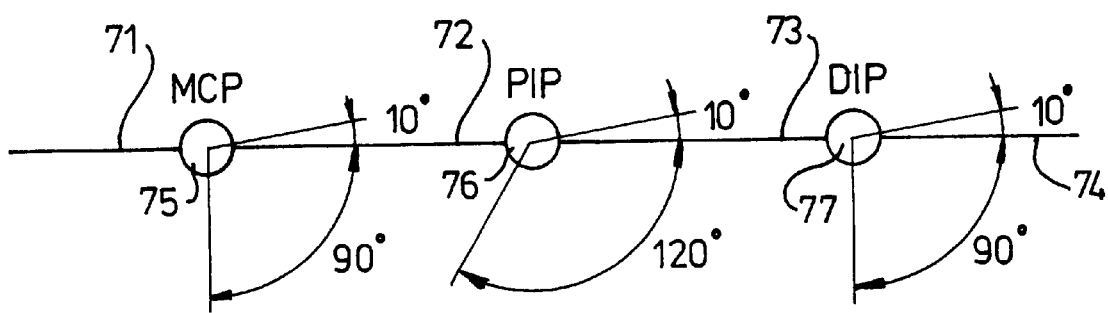
FIG. 6 shows a diagrammatic view of the bones and joints of which a finger is composed.

FIG. 6 provides a highly diagrammatic illustration of the bones of a finger and the joints of a finger. 71 denotes the carpal bones, which for their part comprise a number of small bones and joints, 72 denotes the proximal phalange, 73 denotes the middle phalange and 74 denotes the distal phalange. The joint 75, as indicated by the letters MCP, is the so-called metacarpophalangeal joint, 76 is the so-called PIP (proximal interphalangeal) joint, and 77 is the so-called DIP (distal interphalangeal) joint. The natural freedom of movement of an MCP is, in the upward over-extended direction, generally of the order of 10° and in the downward bending direction of the finger is generally of the order of 90°, both measured with respect to the extended state illustrated in FIG. 6.

The natural freedom of movement of the PIP, again measured with respect to the extended state illustrated in FIG. 6, is generally about 10° in the upward, over-extended direction and approximately 120° in the downward pinching direction.

The natural freedom of movement of the DIP joint, measured with respect to the extended state illustrated in FIG. 6, is generally approximately 10° in the upward, or over-extended direction, and is generally approximately 90° in the downward, bending or pinching direction.

In particular, with regard to the upward over-extending direction, it is advantageous according to the invention if the joint prosthesis has a considerable freedom of rotation in the said direction, for example a freedom of rotation of approximately 15°, i.e. up to a total of 25° with respect to the extended position. This has the advantage that stabilization against upward over-extending is supplied by the natural, or possibly completely or partially artificial, ligaments, so that these will continue to be exercised and will not weaken. Such additional freedom of rotation of the joint prosthesis may also be useful with regard to the downward pinching or gripping movement.

As will be clear from FIG. 3, in the hinged state indicated by solid lines, pivoting of the distal joint prosthesis part 2 in a plane perpendicular to the plane of the drawing in accordance with FIG. 3 will be impeded by the top side 19 of the cylindrical socket 6. Instead of such a mutual tilting or pivoting movement, a moment will then be exerted on the proximal joint prosthesis part 1, which moment seeks to rotate the joint prosthesis part 1 about its longitudinal axis 20. In the case of a PIP joint prosthesis, this rotational moment about axis 20 will then be absorbed by the ligaments of the MCP joint.

What is claimed is:

1. Joint prosthesis comprising a first part (1) with a cylindrical socket (6) and a second part (2) with a cylindrical head (8), the cylindrical head (8) and socket (6) being complementary to one another, in such a manner that together they are able to form a linear hinge having a hinge axis defined by the longitudinal axis (12) of the cylindrical head (8) and socket (6), a radial and a circumferential direction being defined with respect to the hinge axis, characterized:

in that the cylindrical socket (6) extends over at most 180° in the circumferential direction, in that the cylindrical head (8) is provided with a radial thickened section (9) which extends in the circumferential direction, and in that the cylindrical socket (6) is provided with a radial recess (7) which extends in the circumferential direction and in which the radial thickened section (9) can be accommodated.

2. Joint prosthesis according to claim 1, characterized in that the tangent extent of the lines at the free ends of the cylindrical socket define a range of removal directions for removing the head from the socket, the longitudinal direction of a bone to which the cylindrical head is to be attached or of a stem (3) which is to be attached inside a bone and bears the socket (6) at one end lying within the said range of removal directions.

3. Joint prosthesis according to claim 1, in which the first part (1) and the second part (2) each comprise a respective stem, which at one free end respectively bears the cylindrical socket or the cylindrical head, and which can each be attached in a respective bone part, characterized in that the cylindrical socket is oriented in such a way with respect to the stem (3) of the first part (1) that the cylindrical head (8) can be taken out of the cylindrical socket (6) when the two stems are essentially aligned with one another.

4. Joint prosthesis according to claim 1, characterized in that the radial thickened section (9) and radial recess (7) are arranged centrally, as seen in the direction of the hinge axis (12).

5. Joint prosthesis according to claim 1, characterized in that the radial thickened section (9) and/or the radial recess (7) are formed so as to be self-aligning with respect to one another.

6. Joint prosthesis according to claim 5, characterized in that the circumferential sides (14), which extend in the circumferential direction, of the radial thickened section (9) are provided with bevels and/or rounded portions (15).

7. Joint prosthesis according to claim 5, characterized in that the circumferential sides (13), which extend in the circumferential direction, of the radial recess (7) are provided with bevels and/or rounded portions (16).

8. Joint prosthesis according to claim 1, characterized in that the circumferential sides, which extend in the circumferential direction, of the radial thickened section (9) and/or of the radial recess (7) comprise an active circumferential side face which includes an angle of approximately 1° to 10° with a radially oriented transverse plane.

9. Joint prosthesis according to claim 1, characterized in that the cylindrical head (8) is arranged on the end of at least one support arm (10) which extends radially with respect to the cylindrical head (8), and in that one or both longitudinal edge(s) (21) of the cylindrical socket (6) is/are provided, in the area of the at least one support arm (10), with a cutout (17) in which the cross section of the support arm (10) can be completely or partially accommodated.

10. Joint prosthesis according to claim 1, characterized in that the freedom of rotation of the linear hinge in one or both direction(s) of rotation is greater than the associated freedom of rotation of the natural joint which the joint prosthesis is intended to replace.

11. Joint prosthesis according to claim 10, characterized in that the extent to which the said freedom of rotation of the joint prosthesis is greater than that of the natural joint is approximately 5° to approximately 20°.

12. Joint prosthesis according to claim 1, characterized in that the first part (1) and second part (2) are each a metal part.

13. Joint prosthesis according to claim 12, characterized in that the metal parts are made from a chromium-cobalt alloy.

14. Joint prosthesis according to claim 1, characterized in that the first part (1) and second part (2), or at least the contact surfaces of the cylindrical head (8) and cylindrical socket (6), are coated with a coating material.

15. Joint prosthesis according to claim 1, characterized in that the first part (1) and second part (2), or at least their external surfaces, are made from or coated with a material which is compatible with the human body.

16. Joint prosthesis according to claim 1, characterized in that the cylindrical socket (6) extends over at least 160° in the circumferential direction.

17. Joint prosthesis according to claim 1, characterized in that it is a finger joint prosthesis.

18. Joint prosthesis according to claim 1, in which the radial thickened section (9) can be accomodated in the radial recess (7) such that the cylindrical head (8) is in bearing contact inside the cylindrical socket (6).

19. Use of a joint prosthesis according to claim 1 as a finger prosthesis.

* * * * *